United States Patent
Pevere et al.

(10) Patent No.: US 6,479,698 B1
(45) Date of Patent: Nov. 12, 2002

(54) METHOD FOR PREPARING SULPHONATE SALTS

(75) Inventors: Virginie Pevere, Lyons (FR); Pierre Danerol, Lyons (FR)

(73) Assignee: Rhodia Chimie, Boulogne Billancourt (FR)

( * ) Notice: Subject to any disclaimer, the term of this patent is extended or adjusted under 35 U.S.C. 154(b) by 0 days.

(21) Appl. No.: 10/019,051

(22) PCT Filed: Jun. 29, 2000

(86) PCT No.: PCT/FR00/01832

§ 371 (c)(1),
(2), (4) Date: Mar. 20, 2002

(87) PCT Pub. No.: WO01/02348

PCT Pub. Date: Jan. 11, 2001

(30) Foreign Application Priority Data

Jun. 30, 1999 (FR) .............................................. 99 08403

(51) Int. Cl.$^7$ .............................................. C07C 309/06
(52) U.S. Cl. ....................................... 562/113; 562/119
(58) Field of Search ................................. 562/113, 119; 558/54

(56) References Cited

PUBLICATIONS

R.N. Hazeldine et al., *Journal of the Chemical Society*, (1995), pp. 2901–2910, XP002132128.
A.E. Feiring et al., *Journal of Fluorine Chemistry*, vol. 93, No. 2, (Feb. 4, 1999), pp. 93–101.
W. Cen et al., *Inorganic Chemistry*, vol. 27, No. 8, (Apr. 20, 1988), pp. 1376–1377.

*Primary Examiner*—Joseph K. McKane
*Assistant Examiner*—Joseph Murray
(74) *Attorney, Agent, or Firm*—Burns, Doane, Swecker & Mathis, L.L.P.

(57) ABSTRACT

The invention concerns a method for preparing sulphonate salts, alkaline or alkaline-earth, corresponding to anion of general formula (I):$(R-CF_2-SO_3^-)_n$, through alkaline hydrolysis of sulphonyl chlorides corresponding to formula (II). The invention is characterized in that it comprises at least a step which consists in alkaline hydrolysis of sulphonyl chloride carried out in the presence of a phase-transfer agent.

17 Claims, No Drawings

METHOD FOR PREPARING SULPHONATE SALTS

This application is a 371 of PCT/FR00/01832 filed Jun. 29, 2000.

The present invention relates to a process for preparing sulfonate salts via alkaline hydrolysis of the corresponding sulfonyl chlorides.

The conventional method for obtaining a sulfonate salt from a sulfonyl chloride consists in carrying out the hydrolysis of the sulfonyl chloride using inexpensive bases, such as alkali metal or alkaline earth metal carbonates or hydroxides, e.g. sodium hydroxide. However, the literature includes only a few cases of alkaline hydrolysis of sulfonyl chloride by this kind type of bases: mention may be made, among these rare examples, of R. N. Haszeldine (J. Chem. Soc., 2901 (1955)), who describes a quantitative alkaline hydrolysis of trifluoromethanesulfonyl chloride by 15% sodium hydroxide, i.e. by a sodium hydroxide solution with a relatively low concentration.

It should be noted that the hydrolysis of a sulfonyl chloride, and in particular of a (per)fluorinated sulfonyl chloride, is generally difficult to carry out, especially because of the covalent nature of the $SO_2$—Cl bond, and in view of the fact that these substrates are generally better oxidizing agents than electrophiles. In this respect, it should actually be emphasized that similar compounds, such as sulfuryl chloride $SO_2Cl_2$, are commonly used as chlorinating agents. Generally, sulfonyl chlorides are therefore often not very reactive with respect to the hydrolysis reaction.

Consequently, the problem encountered during the alkaline hydrolysis of a sulfonyl chloride is as follows: the hydrolysis reaction of the sulfonyl chloride is a reaction which, on the one hand, intrinsically has a significant exothermic nature and which, on the other hand, is characterized by significant inertia, due to the fact that the reactants are present in two, separate phases, which accentuates the exothermicity of the reaction. This inertia does not give rise to any complication during the hydrolysis of small amounts and/or with dilute alkaline solutions, such as those described in the literature; however, it raises real safety problems as soon as attempts are made to carry out the reaction with higher concentrations of base and/or on industrial amounts: this is because the inertia of the reaction then leads to a buildup of sulfonyl chloride during the reaction which can represent up to 20% of the amount of sulfonyl chloride introduced and which, in conjunction with the high intrinsic exothermicity of the hydrolysis reaction, can lead to runaway of the reaction.

To avoid such problems, the only currently existing solution consists in carrying out the alkaline hydrolysis by means of a dilute hydroxide solution, which involves removing the water by additional distillation stages, harmful in terms of industrial productivity.

The aim of the present invention is specifically to provide a method for the preparation of sulfonate salts which are simultaneously inexpensive, fast and reliable, by carrying out the alkaline hydrolysis of a sulfonyl chloride with a concentrated basic solution, but while avoiding the problem of buildup of the sulfonyl chloride due to the inertia of the reaction.

More specifically, the resent invention relates to a process for preparing an alkali metal or alkaline earth metal sulfonate salt corresponding to the anion of general formula (I):

$$R-CF_2-SO_3^{31}$$ (I), wherein R is:

(a) a hydrogen atom;
(b) a halogen, preferably a light halogen (that is to say, with an atomic number at most equal to that of chlorine), and more preferably fluorine;
(c) an alkyl chain optionally substituted by one or more halogen atom(s);
(d) an alkenyl chain optionally substituted by one or more halogen atom(s);
(e) an aryl group which is optionally substituted by one or more halogen atom(s) and which can comprise one or more heteroatoms;
(f) an arylalkyl group optionally substituted by one or more halogen atom(s), it being possible for the aryl group to comprise one or more heteroatoms; or
(g) a sulfonyl heavy halide group, with it being possible for R, when it is a group as defined in (c), (d), (e) and (f), to be substituted by a sulfonyl heavy halide group, said sulfonate salt being obtained from a sulfonyl chloride of general formula (II)

$$R-CF_2-SO_2Cl$$

wherein R is as defined above, said process comprising at least one stage of alkaline hydrolysis of the sulfonyl chloride (II) in the presence of at least one compound acting as a phase transfer agent.

The R group present in the sulfonyl chlorides employed in the process of the invention is preferably an electron-withdrawing group, that is to say a radical with a σp value generally greater than 0, preferably greater than 0.1 and advantageously at least equal to 0.5.

R is advantageously a fluorine atom or a perfluoroalkyl radical $R_f$ optionally substituted by a sulfonyl heavy halide group.

Within the meaning of the invention, a sulfonyl heavy halide group refers to a group carrying a sulfonyl halide functional group or a halogen and chlorine or bromine and preferably chlorine and for which the carbon atom adjoining the sulfur atom is perhalogenated by halogens with an atomic number at most equal to that of chlorine and is preferably perfluorinated. This group can have from 1 to 10 carbon atoms.

Thus, the claimed process s especially suitable for preparing alkali metal or alkaline earth metal sulfonate salts which exhibit at least one, indeed even two, sulfonyl group (s), the carbon atom(s) adjoining the sulfur atom(s) being perfluorinated.

These bisulfonate compounds can be useful in particular for preparing polymeric compounds or alternatively cyclic compounds, when the number of linking units separating the two sulfonate functional groups is 2, 3 or 4. The linking units which separate the two sulfonate functional groups are advantageously $CF_2$ linking units.

Furthermore, it should be pointed out that the, carbonaceous chains present in the sulfonyl chlorides employed in the process of the invention are preferably saturated chains, so as in particular to avoid phenomena of untimely polymerization. Furthermore, the sulfonyl chlorides employed in the process of the invention generally comprise a total carbon atom number advantageously of less than 30.

Within the meaning of the present invention, the term "phase transfer agent" denotes a compound capable of compensating for the inertia of the hydrolysis reaction and of preventing the problem of the buildup of the sulfonyl chloride due to the fact that the reactants are found in two separate phases.

This phase transfer agent may be either of cryptant type, such as crown ethers, or of onium type, or an alcohol.

Thus, according to a first aspect of the invention, the role of phase transfer agent is played by a phase transfer agent of onium cation type.

Oniums are compounds with names, in the nomenclature, comprising the sequence of letters "onium" as affix, generally as suffix. They are semimetallic compounds, in particular from the nitrogen column and from the sulfur column, which are sufficiently substituted to carry a positive charge. Thus, the atoms from the nitrogen column, when they are substituted four times by a hydrocarbonaceous radical, constitute oniums.

Thus, quaternary ammoniums or quaternary phosphoniums can be used as phase transfer agent.

Sulfoniums (tertiary in their case) themselves also constitute phase transfer agents, but they are less advantageous, since they are relatively more unstable than the others.

The oniums used as phase transfer agent are known to a person skilled in the art.

The most commonly used are tetraalkylammoniums and tetraalkyl- or tetraphenylphosphoniums. The latter exhibit, however, the disadvantage of being relatively expensive.

The preferred phase transfer agents among said, onium cations are tetraalkylammonium comprising saturated, unsaturated or aromatic hydrocarbonaceous chains comprising a total of 4 to 28 carbon atoms, preferably of 4 to 16 carbon atoms.

To avoid β-elimination reactions, the most widely used onium is tetramethylammonium, although it is relatively unstable from approximately 150° C.; mention may also be made of benzyltrimethylammonium.

The onium cation is preferably employed in an amount representing from 1 to 20 mol % with respect to the total number of sulfonyl chloride functional group(s) present on the compound of formula II, more preferably from 1 to 5 mol %.

According to a second aspect of the invention, which is a preferred embodiment, an alcohol, in particular a linear or branched and aliphatic or aromatic alcohol, comprising from 1 to 10 carbon atoms, preferably more than 2 carbon atoms, is used as phase transfer agent, the most preferably used alcohol being selected from isopropanol, ethanol, benzyl alcohol, isobutanol, n-propanol and sec-butanol.

In fact, any alcohol is suitable as phase transfer agent according to the present invention, insofar as it is incapable of participating in side reactions, in particular in the formation of an ether in a sufficient amount to threaten the reliability of the process.

In this respect, it is surprising to find that a primary or secondary alcohol can be employed in the basic hydrolysis process of the invention. This is because the sulfonyl chloride employed is generally a better oxidizing agent than electrophile, which should lead to the oxidation of the alcohol employed, very particularly in the context of the use of perfluorinated sulfonyl chlorides, the oxidizing nature of which is very pronounced. Furthermore, it should be emphasized that, among the alcohols preferably employed, isopropanol is known as being a good reducing agent.

Whatever its nature, the alcohol used is preferably employed in a proportion of 0.05 to 1 molar equivalent with respect to the number of sulfonyl chloride functional group(s) present on the compound of formula II, more preferably in a proportion of 0.1 to 0.2 molar equivalent.

Said alcohol used as phase transfer agent can optionally be partially present in the form of the alkoxide ion in the basic hydrolysis medium.

The term "alkaline hydrolysis" is understood to denote, within the meaning of the present invention, hydrolysis by means of a basic solution of an alkali metal or alkaline earth metal hydroxide or of a solution of carbonate salts.

The alkali metal or alkaline earth metal hydroxide solutions which are very particularly suitable for the present invention are solutions of a metal hydroxide of general formula III:

$$(M)(OH)_n \qquad (III),$$

where

M is an alkali metal or alkaline earth metal, and preferably an alkali metal; and n is an integer:
  equal to 1 in the case where M is an alkali metal,
  equal to 2 in the case where M Is an alkaline earth metal, in a solvent of hydroxylated type, the preferred solvent being water, a preferred alkali metal hydroxide solution being an aqueous sodium hydroxide solution.

The solutions of carbonate salts according to the present invention are solutions of a metal carbonate of general formula (IV):

$$(M)_n(CO_3) \qquad (IV),$$

where

M is an alkali metal or alkaline earth metal, preferably an alkali metal or magnesium, and advantageously sodium; and n is an integer:
  equal to 1 in the case where M is an alkaline earth metal,
  equal to 2 in the case where M is an alkali metal, in a solvent of hydroxylated type, the preferred solvent being water.

As emerges from the examples presented below, the alcohol acts, like the onium salt, as a phase transfer agent between the alkaline solution and the sulfonyl chloride, even if the nature of this phase transfer remains to be specifically defined. Measurements of heats of reaction given off during alkaline hydrolyses carried out in the presence of an alcohol in any case undoubtedly reveal a sharp reduction in the buildup of the sulfonyl chloride during the reaction in comparison with measurements carried out in the absence of phase transfer agent: the presence of alcohol leads to a marked decrease in the delay observed in the evolution of the heat of reaction, that is to say a substantial increase in the rate of the alkaline hydrolysis reaction.

The preferred process according to the invention comprises a stage of gradual addition of sulfonyl chloride at atmospheric pressure to a mixture comprising at least:
  said alkaline solution of hydroxide or of carbonate, and
  said phase transfer agent composed of a compound of cryptant type, of a compound of onium salt type or of an alcohol.

Preferably, the alkaline solutions are aqueous solutions and are employed at concentrations of greater than 20% by mass, which makes it possible to eliminate the stages of distillation of water. Furthermore, in order to be able to carry out correct stirring, this concentration, which should not be too high in order to avoid an excessively high viscosity, is more preferably between 20 and 30% by mass.

In order to carry out a quantitative reaction, whatever the nature of the base used, the base is generally employed in an amount close to the stoichiometry of the reaction, that is to say in an amount of the order of two molar equivalents with respect to the number of sulfonyl chloride functional group(s) present on the compound of formula II, advantageously in a proportion of 1.8 to 2.5 molar equivalents, and preferably in an amount equal to 2 molar equivalents, with respect to the number of sulfonyl chloride functional group (s) present.

Whether an alcohol or an onium salt is used, it may be considered that the presence of the phase transfer agent makes it possible to decrease the duration of the hydrolysis reaction by approximately 50%, which, first, improves the efficiency of the process but also makes it possible to operate under enhanced conditions of safety by preventing the problems related to the buildup of the sulfonyl chloride. Be that as it may, as a result of the high intrinsic exothermicity of the reaction, the hydrolysis can be carried out while cooling the reaction medium using, for example, an ice bath. This is because it is generally preferable for the temperature of the reaction medium to be maintained between −10° C. and 50° C. during the alkaline hydrolysis. It is advantageously preferable for this temperature not to exceed 30° C. In the specific case of the use of $CF_3SO_2Cl$ in the alkaline hydrolysis stage, it is furthermore preferable for this temperature to remain. below 20° C., in particular as a result of the low boiling point (29° C.) of this compound. However, if it is desired to implement the process of the invention at temperatures greaer than or equal to the boiling point of the sulfonyl chloride used, it is possible to carry out the reaction at a pressure greater than atmospheric pressure, for example in a closed chamber, and generally, in this case, at the autogeneous pressure of the reaction medium at the temperature at which it is desired to operate.

However, it should be clearly emphasized that the limitation on the rise in the temperature is generally due essentially to the presence of a phase transfer agent, which limits the phenomena of buildup of the sulfonyl chloride, very particularly in the case of the use of large amounts of reactant.

Furthermore, it should also be noted that the specific presence of the phase transfer agent makes it possible to carry out the process of the invention on an industrial scale without risk of overheating or of runaway of the reaction. Thus, the amounts of sulfonyl chloride employed in the process of the invention can, in the general case, reach amounts of greater than 1000 mol, indeed even greater than 5000 mol.

It should also be noted that the process of the invention lends itself to a continuous embodiment.

According to one aspect of the invention, the alkaline hydrolysis process makes It possible to obtain said sulfonate salt in solution, preferably in aqueous solution, for example for a direct use in situ of said salt as reaction intermediate, in particular for the synthesis of the corresponding sulfonic acid, these operations coming within the competence of a person skilled in the art.

According to another aspect of the invention, the process of preparation of the sulfonate salt makes it possible to obtain the salt in the solid form, in particular by selective precipitation and/or by concentrating to dryness, for example for an optionally subsequent use of said salt as reaction intermediate, in particular for the synthesis of the corresponding sulfonic acid, in a way also known per se.

The examples set out below illustrate the present invention. They are given by way of explanation of the description and should not under any circumstances limit the scope thereof.

EXAMPLE 1

Buildup Profiles

Example 1 presents three type of buildup profile observed in the case of the alkaline hydrolysis of $CF_3SO_2Cl$ by solutions (A), (B) and (C) characterized by the following compositions (the percentages indicated correspond to percentages by mass):

(A): 30% aqueous sodium hydroxide solution (B): 20% aqueous sodium hydroxide solution (C): 20% aqueous sodium hydroxide solution+ isopropanol (0.2 molar equivalent).

The buildup, expressed in kJ/mol, is calculated from the amount of heat given off by the hydrolysis reaction at the end of a time t: it corresponds to the difference between the expected amount of heat given off and the amount of heat actually given off.

The results obtained are combined in Table 1 below:

TABLE 1

| | | Buildup (kJ/mol) | | |
|---|---|---|---|---|
| Time (min) | Number moles charged | (A) 30% NaOH | (B) 20% NaOH | (C) 20% NaOH + isopropanol |
| 0 | 0 | | | |
| 5 | 0.08 | 243 | 19.5 | 1.8 |
| 10 | 0.066 | 237 | 29.6 | 2.2 |
| 30 | 0.33 | 221 | 73 | 7.3 |
| 40 | 0.42 | 210 | 82 | 8.7 |
| 60 | 0.66 | 204 | 105 | 26.3 |
| 80 | 0.88 | 188 | 149 | 32 |
| 125 | 1.38 | 150 | 136 | 13 |
| 150 | 1.6 | 74 | 69 | 11 |
| 180 | 2 | 63 | 60 | 11 |

Comparison of the profiles obtained with the solutions (A) and (B) (respectively 30% and 20% by mass aqueous sodium hydroxide solutions) shows the influence of the concentration of hydroxide on the buildup: in fact, the buildups observed with a 30% by mass solution are more than 200 kJ/mol from the beginning of the experiment and lasting throughout the first hour of the hydrolysis, which raises significant problems of safety, in particular when operating on industrial amounts, whereas, with a 20% solution, the buildup is lower by an order of magnitude from the start and, even on combining the delay due to the inertia of the reaction, the buildup finally only reaches maximum values of the order of 150 kJ/mol, for a duration of approximately 40 minutes. Be that as it may, these values nevertheless remain very high and the results obtained with the solution (C) (20% by mass aqueous sodium hydroxide solution and isopropanol (0.2 equivalent)) show the whole advantage of the present invention: the buildups observed in the presence of isopropanol are decreased by an order of magnitude with respect to those produced with the solution (B) devoid of phase transfer agent, and the maximum buildup observed is only of the order of 30 kJ/mol, which greatly reduces the risks usually accompanying the use of concentrated alkaline solution.

The two following examples set out two processes for the preparation of sodium trifluoromethanesulfonate (more commonly known as sodium triflate) by alkaline hydrolysis, using an alcohol as phase transfer agent, according to the present invention.

EXAMPLE 2

Preparation of Sodium Triflate by Alkaline Hydrolysis in the Presence of Isopropanol 120 g of 20% sodium hydroxide (i.e. 0.6 mol of NaOH) and 3.6 g of isopropanol (0.06 mol) are charged to a 200 ml reactor. The addition of trifluoromethanesulfonyl chloride (50.5 g, i.e. 0.3 mol) is carried out over 1 h 45 while maintaining the reaction medium at 25° C. by cooling with a water/ice mixture.

After adding the reactant, the reaction medium is kept stirred for 30 min and then acidified with a 36% HCl solution to a pH=6.

The homogeneous medium obtained is concentrated at 70° C. under 100 mbar until a weight of 162 g is obtained. The precipitate formed is filtered off at 20° C.

The filtrate obtained is subsequently concentrated to dryness and 57 g of a white solid are obtained, which solid is composed of 43.3 g of sodium trifluoromethanesulfonate (sodium triflate), 5.2 g of sodium chloride and residual water.

EXAMPLE 3
Preparation of Sodium Triflate by Alkaline Hydrolysis in the Presence of Ethanol 48 g of 50% by mass aqueous sodium hydroxide (i.e. 0.6 mol NaOH) and 80 ml of ethanol are charged to a 200 ml reactor. The addition of trifluoromethanesulfonyl chloride (50.5 g, i.e. 0.3 mol) is carried out over 1 h 00 without exceeding 30° C. by cooling with a water/ice mixture. The precipitation of NaCl is immediate. After addition, the reaction medium is kept stirred for 2 h and then cooled to 5° C. The precipitate is filtered off at this temperature (dry weight=17.3 g). A filtrate weighing 125 g is obtained, which filtrate comprises 40.6 g of sodium triflate and 0.8 g of sodium chloride.

The quantitative aspect of the reactions and in particular the speed with which the reactions are carried out (overall reaction time of 2 h 15 for Example 2 and of 3 h 00 for Example 3), and the completely safe aspect of the handling (temperature not exceeding 25° C. in Example 2 and not exceeding 30° C. in Example 3), despite the high concentrations of the sodium hydroxide solutions employed and the speed with which the addition is carried out (1 h 45 for Example 2 and only 1 h 00 for Example 3), should be noted in these two examples.

EXAMPLE 4
Preparation of Sodium Triflate by Alkaline Hydrolysis in the Presence of a Phase Transfer Agent of Onium Type This final example relates to a process for the preparation of sodium triflate by alkaline hydrolysis according to the present invention using a cation of onium type as phase transfer agent.

80 g of 30% aqueous sodium hydroxide (corresponding to 0.6 mol of NaOH) and 1.25 g of benzyltrimethylammonium chloride are placed in a 250 ml reactor. 50.5 g (0.3 mol) of trifluoromethanesulfonyl chloride are subsequently added over 1 h 30 while stirring at ambient temperature.

After stirring for 2 hours the medium is filtered at 20° C. The aqueous phase is composed of 46.1 g of sodium triflate (0.27 mol).

It may also here be observed that the overall reaction time is sufficiently low (3 h 30) and that, even if the addition is carried out over only 1 h 30, the reaction is carried out at ambient temperature without presenting safety problems.

What is claimed is:

1. A process for producing an alkali metal or alkaline earth metal sulfonate salt corresponding to the anion of general formula (I):

$$R-CF_2-SO_3^- \qquad (I),$$

wherein R is:
(a) a hydrogen atom;
(b) a halogen;
(c) an alkyl chain optionally substituted by one or more halogen atom(s);
(d) an alkenyl chain optionally substituted by one or more halogen atom(s);
(e) an aryl group which is optionally substituted by one or more halogen atom(s) and which can comprise one or more heteroatoms;
(f) an arylalkyl group optionally substituted by one or more halogen atom(s), it being possible for the aryl group to comprise one or more heteroatoms; or
(g) a sulfonyl heavy halide group, with it being possible for R, when it is a group as defined in (c), (d), (e) and (f), to be substituted by a sulfonyl heavy halide group, said sulfonate salt being obtained from a sulfonyl chloride of general formula (II)

$$R-CF_2-SO_2Cl$$

wherein R is as defined above, said process comprising at least one stage of alkaline hydrolysis of the sulfonyl chloride (II) in the presence of at least one compound acting as a phase transfer agent, said compound being either a cryptant, or a cation of onium type, or an alcohol.

2. The process as claimed in claim 1, wherein said phase transfer agent is an onium cation.

3. The process as claimed in claim 2, wherein said onium cation is a tetraalkylammonium cation comprising saturated, unsaturated or aromatic hydrocarbonaceous chains comprising a total of 4 to 28 carbon atoms.

4. The process as claimed in claim 2, wherein the onium used is benzyltrimethylammonium or tetramethylammonium.

5. The process as claimed in claim 2, comprising 1 to 20 mol % of onium salt with respect to the number of sulfonyl chloride functional group(s) present on the compound of formula (II).

6. The process as claimed in claim 1, wherein said phase transfer agent is an alcohol.

7. The process as claimed in claim 6, wherein said alcohol is a linear or branched and aliphatic or aromatic alcohol comprising from 1 to 10 carbon atoms.

8. The process as claimed in claim 6, wherein the alcohol used is selected from the group consisting of isopropanol, ethanol and benzyl alcohol, isobutanol, n-propanol and sec-butanol.

9. The process as claimed in claim 6, comprising 0.05 to 1 equivalent of alcohol with respect to the number of sulfonyl chloride functional group(s) present on the compound of formula (II).

10. The process as claimed in claim 1, wherein the alkaline hydrolysis of the sulfonyl chloride (II) is carried out by means of a base selected from the group consisting of alkali metal or alkaline earth metal hydroxides and carbonates.

11. The process as claimed in claim 10, wherein said base is a metal hydroxide.

12. The process as claimed in claim 11, wherein the metal hydroxide is present in the form of a solution with a concentration of greater than 20%.

13. The process as claimed in claim 11, wherein the metal hydroxide used is sodium hydroxide, potassium hydroxide or lithium hydroxide.

14. The process as claimed in claim 1, wherein the amount of base employed is from 1.8 to 2.5 molar equivalents with respect to the number of sulfonyl chloride functional group(s) present on the compound of formula (II).

15. The process as claimed in claim 1, wherein the salt obtained is sodium triflate $CF_3SO_3Na$.

16. The process as claimed in claim 1, wherein said alkali metal or alkaline earth metal salt of general formula (I) is obtained in the form of an aqueous solution and is converted in situ to result in the corresponding sulfonic acid.

17. The process as claimed in claim 1, wherein said alkali metal or alkaline earth metal salt is obtained in the form of a solid.

* * * * *